(12) United States Patent
Wong

(10) Patent No.: US 9,939,442 B2
(45) Date of Patent: Apr. 10, 2018

(54) SALIVARY BIOMARKERS FOR GASTRIC CANCER DETECTION

(75) Inventor: David T. Wong, Beverly Hills, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 13/607,236

(22) Filed: Sep. 7, 2012

(65) Prior Publication Data

US 2013/0065769 A1 Mar. 14, 2013

Related U.S. Application Data

(60) Provisional application No. 61/532,210, filed on Sep. 8, 2011.

(51) Int. Cl.
| | | |
|---|---|---|
| C40B 30/00 | (2006.01) | |
| C40B 30/04 | (2006.01) | |
| G01N 33/574 | (2006.01) | |
| C12Q 1/68 | (2018.01) | |
| C40B 20/00 | (2006.01) | |
| C40B 40/06 | (2006.01) | |

(52) U.S. Cl.
CPC ..... *G01N 33/57446* (2013.01); *C12Q 1/6886* (2013.01); *C12Q 2600/158* (2013.01); *G01N 2800/52* (2013.01)

(58) Field of Classification Search
CPC ......... C40B 30/04; C40B 20/00; C40B 40/10; C40B 40/06
USPC ............................................. 506/9, 16, 18, 2
See application file for complete search history.

(56) References Cited

U.S. PATENT DOCUMENTS

| | | | | |
|---|---|---|---|---|
| 2009/0047667 | A1* | 2/2009 | Wong | 435/6 |
| 2009/0131356 | A1* | 5/2009 | Bader et al. | 514/44 |
| 2009/0163434 | A1* | 6/2009 | Bader et al. | 514/44 |
| 2009/0317820 | A1* | 12/2009 | Wong | C12Q 1/6809 435/6.14 |
| 2011/0177965 | A1* | 7/2011 | Hoshen | C12N 15/111 506/9 |

FOREIGN PATENT DOCUMENTS

| | | | |
|---|---|---|---|
| EP | 2327799 | A1 * | 6/2011 |
| WO | WO 2009100029 | A1 * | 8/2009 |
| WO | WO 2010108192 | A1 * | 9/2010 |
| WO | WO 2010151789 | A1 * | 12/2010 |

OTHER PUBLICATIONS

Wu et al., Diagnostic Model of Saliva Protein Finger Print Analysis of Patients with Gastric Cancer, World J. Gastroenterol., 2009, 15(7), 865-870.*

Pollock et al., Hindawi Publishing Corporation, Induction of Metatstatic Gastric Cancer by Peroxisome Proliferator-Activated Receptor Delta Activation, PPAR Research, 2010, Article ID 571783, 1-12.*
Shah et al., A Review on Salivary Genomic and Proteomics Biomarkers in Oral Cancer, Ind. J. Biochem., published online Aug. 2011, 26(4), 326-334.*
Xia et al., miR-15b and miR-15 Modulate Multidrug Resistance by Targeting BCL2 in Human Gastric Cancer Cells, Int. J. Cancer, 2008, 123, 372-379.*
Conde et al., DMBT1 Is Frequently Downregulated in Well-Differentiated Gastric Carcinoma But More Frequently Upregulated Across Various Gastric Cancer Types, Int. J. of Oncology, 2007, 30, 1411-1446.*
Nakai et al., A Case of Isolated Pancreatic Metasasis of Gastric Cancer Presenting Problematic Discrimination From Gastropancreaic Double Cancer, Hepto-gastroenterology, 2004, 51(59), Abstract.*
Nakai et al., A Case of Isolated Pancreatic Metastasis of Gastric Cancer Presenting Problematic Discrimination From Gastropancreatic Double Cancer, Hepato-Gastroenterology, 2004, 51(59), 1571-1574.*
Cui et al., Molecular Cloning and Characterization of a Novel Esophageal Cancer Related Gene, International Journal of Oncology, 2010, 37, 1521-1528.*
Kupfer et al, Examining Smoking-Induced Differential Gene Expression Changes in Buccal Mucosa, Final Report, Federal Aviation Administration, 2010, 1-22.*
Conde et al., DMBT1 is Frequently Downregulated in Well-Differentiated Gastric Carcinoma But More Frequently Upregulated Across Various Gastric Cancer Types, International Journal of Oncology, 2007, 30, 1441-1446.*
Opinion, *Ariosa Diagnostics, Inc.* v. *Sequenom, Inc.* and , United States Court of Appeals for the Federal Circuit, 2015, 1-21.*
*Genetic Tehcnologies Limited* v. *Merial L.L.C.*, Opinion of the United States Court of Appeals for the Federal Circuit, 2016, 1-20.*
Anon. 'GeneChip® Human Genome Arrays' Affymetrix Data Sheet [retrieved on Jun. 30, 2014]. Retrieved from Internet <http://media.affymetrix.com/support/technical/datasheets/human_datasheet.pdf> copyright 2003-2004.
Li et al., Salivary transcriptome diagnostics for oral cancer detection; Clinical Cancer Research, vol. 10, pp. 8442-8450, 2004.
"GeneChip Human Genome Arrays—The Most Comprehensive Coverage of All Well-Substantiated Genes in the Human Genome." Affymetrix Data Shee (2004).

(Continued)

*Primary Examiner* — Amy M Bunker
(74) *Attorney, Agent, or Firm* — Riverside Law LLP

(57) ABSTRACT

Disclosed herein are biomarkers related to gastric cancer. The presently identified salivary biomarkers create the basis for a gastric cancer detection bioassay with sensitivity and specificity. Means and methods for evaluating the data generated using multiple biomarkers in order to validate findings and further use of the multiplexed gastric cancer assay in clinical, diagnostic and therapeutic uses is also included.

3 Claims, No Drawings

(56) References Cited

OTHER PUBLICATIONS

Gu et al., "Bacterial 16S rRNA/rDNA Profiling in the Liquid Phase of Human Saliva," The Open Dentistry Journal, vol. 3, pp. 80-84 (2009).

Conrads et al., "Testing for Marker Bacteria in Progressive Periodontitis: The European Experience" Infectious Diseases in Clinical Practice, vol. 10, pp. 481-487 (2001).

* cited by examiner

US 9,939,442 B2

SALIVARY BIOMARKERS FOR GASTRIC CANCER DETECTION

CROSS-REFERENCES TO RELATED APPLICATIONS

The present application claims priority to U.S. Ser. No. 61/532,210, filed Sep. 8, 2011, herein incorporated by reference in its entirety.

STATEMENT OF GOVERNMENT RIGHTS

This invention was made with U.S. Government support under Grant No. DE016275 awarded by the National Institutes of Health. The U.S. Government has certain rights in the invention.

BACKGROUND

Gastric cancer is a highly aggressive and lethal malignancy. On a global basis, gastric cancer is the second leading cancer cause of death. Every year nearly 700,000 people die from the disease. Asian countries, such as Japan and Korea, have particularly high incidents of gastric cancer. For example, it is estimated that gastric cancer causes more than 16% of the male deaths in Korea and Japan.

Both heredity and environmental factors play roles in the development of gastric cancer. First-generation offspring of gastric cancer patients and people with blood type A are at increased risk of gastric cancer. There also appears to be a correlation between a relatively high salt diet and gastric cancer. A high incidence of gastric cancer is reported in countries in which salted fish is a dietary staple such as Korea, Japan, Finland, and Iceland.

In addition to heredity and diet, infection with *Helicobacter pylori* (*Campylobacter pyloridis*) is a risk factor for developing gastric cancer.

Gastric cancer may exhibit a wide range of symptoms and is often confused with other more benign digestive illnesses. Gastric cancer often goes undiagnosed until detected in an advanced state thereby limiting ameliorative treatment options.

Currently, a diagnosis of gastric cancer is made by gastrointestinal X-ray examination and endoscopic examination both of which have particular limitations. X-ray examination can miss small lesions while endoscopy requires the patient to undergo anesthesia. Both of these methods require highly trained specialists and are impractical as a general screening method.

There remains a need for a rapid, minimally invasive screening assay for gastric cancer.

BRIEF SUMMARY OF THE INVENTION

Survival of cancer patients is greatly enhanced when the cancer is detected and treated early. In the case of gastric cancer, patients diagnosed with early stage disease have 5-year survival rates of 90%, compared to approximately 10% for patients diagnosed with advanced disease. However, the vast majority of gastric cancer patients currently present with advanced disease. Therefore, developments that lead to early diagnosis of gastric cancer can lead to an improved prognosis for the patients.

Identification of specific cancer-associated markers in biological samples, including body fluids, for example, saliva, can provide a valuable approach for the early diagnosis of cancer, leading to early treatment and improved prognosis. Specific cancer markers also can provide a means for monitoring disease progression, enabling the efficacy of surgical, radiotherapeutic, and chemotherapeutic treatments to be tracked.

Accordingly, in some embodiments of the invention, a method for diagnosing gastric cancer in a subject is provided. The method comprises a) providing a saliva sample from the subject; b) analyzing the saliva sample with an assay that specifically detects at least twelve biomarkers in the saliva sample, wherein the twelve biomarkers are Annexin 1 (ANXA1), Cystatin/Stefin B (CSTB), Semaphorin 4B (SEMA4B), S100 calcium binding protein A10 (S100A10), Periplakin (PPL), Serine peptidase inhibitor, Kazal type 7 (SPINK7), EROL-like, RAN binding protein 9 (RANBP9), CD24, Keratin 6A (KRT6A), Keratin 4 (KRT4), and eukaryotic translation initiation factor 3 subunit G (EIF3G); c) comparing the subject biomarker profile with a control biomarker profile wherein a statistically significant difference between the subject biomarker profile and the control biomarker profile is indicative of gastric cancer; and d) effectuating a treatment regimen based thereon. In an embodiment, the control biomarker profile is derived from a patient with gastric cancer. In an embodiment, the biomarker types comprise mRNA biomarkers. In an embodiment, the mRNA is detected by mass spectroscopy, PCR microarray hybridication, thermal sequencing, capillary array sequencing, or solid phase sequencing.

In some embodiments, a method for diagnosing gastric cancer in a subject is provided. The method comprises a) providing a saliva sample from the subject; b) analyzing the saliva sample with an assay that specifically detects at least three biomarkers in the saliva sample, wherein the three biomarkers are triophosphate isomerase 1 (TPL1), Cystatin-B (CSTB), deleted in malignant brain tumors 1 protein (DMBT1); c) comparing the subject biomarker profile with a control biomarker profile wherein a statistically significant difference between the subject biomarker profile and the control biomarker profile is indicative of gastric cancer; and d) effectuating a treatment regimen based thereon. In an embodiment, the control biomarkers profile is derived from a patient with gastric cancer. In an embodiment, the biomarkers types comprise polypeptide biomarkers. In an embodiment, the polypeptide is detected by ELISA, Western blot, flow cytometry, immunofluorescence, immunohistochemistry, or mass spectroscopy.

In some embodiments, a method for diagnosing gastric cancer in a subject is provided. The method comprises a) providing a saliva sample from the subject; b) analyzing the saliva sample with an assay that specifically detects at least four biomarkers in the saliva sample, wherein the four biomarkers are *Neisseria* sp strain (B33KA_ot020_Y56, *Eikenella corrodens* and *Kingella dentriflicans* and sp clone (DE012_0t012_577_582_AD98, *Streptococcus australis* and sp clone (FN04_ot65_073_Ab83), *Fusobacterium* all species (AD99); c) comparing the subject biomarker profile with a control biomarker profile wherein a statistically significant difference between the subject biomarker profile and the control biomarker profile is indicative of gastric cancer; and d) effectuating a treatment regimen based thereon. In some embodiments, the control biomarker profile is derived from a patient with gastric cancer. In some embodiments, the biomarker types comprise bacterial markers.

In some embodiments, a method for diagnosing gastric cancer in a subject is provided. The method comprises a) providing a saliva sample from the subject; b) analyzing the saliva sample with an assay that specifically detects at least six biomarkers in the saliva sample, wherein the six biomarkers are miR-140-5p, miR-374a, miR-454, miR-15b, miR-28-5p, or miR-301a; c) comparing the subject biomarker profile with a control biomarker profile wherein a statistically significant difference between the subject biomarker profile and the control biomarker profile is indicative of gastric cancer; and d) effectuating a treatment regimen based thereon. In an embodiment, the control biomarker profile is derived from a patient with gastric cancer. In an embodiment, the biomarker types comprise bacterial markers.

In some embodiments, a diagnostic assay for gastric cancer is provided, the assay encompassing isolating a saliva sample from a subject, detecting at least two biomarker types in the saliva sample, wherein the biomarker types comprise an mRNA biomarker, a polypeptide biomarker, a bacterial marker and/or a micro-RNA marker, wherein the mRNA biomarker comprises at least one of ANXA1, CSTB, SEMA4B, S100A10, PPL, SPINK7, EROL-like, RANBP9, CD24, KRT6A, KRT4, EIF3G, the polypeptide biomarker comprises at least one of TPL1, CSTB, DMBT1, the bacteria marker comprises at least one of *Neisseria* sp strain (B33KA_ot020_Y56, *Eikenella corrodens* and *Kingella dentriflicans* and sp clone (DE012_0t012_577_582_AD98, *Streptococcus australis* and sp clone (FN04_ot65_073_Ab83), *Fusobacterium* all species (AD99), and the micro-RNA marker comprises at least one of miR-140-5p, miR-374a, miR-454, miR-15b, miR-28-5p, or miR-301a, comparing the levels of the detected biomarker types in the saliva sample with a control level of the biomarker types, wherein a statistically significant difference between the detected biomarker types in the saliva sample and the control level is indicative of gastric cancer and effectuating a treatment regimen based thereon.

In some embodiments, a method of assessing the efficacy of a therapy on a subject is provided encompassing analyzing a first saliva sample from the subject with an assay that specifically detects at least two biomarkers selected from the group consisting of Annexin 1 (ANXA1), Cystatin/Stefan B (CSTB), Semaphorin 4B (SEMA4B), S100 calcium binding protein A10 (S100A10), Periplakin (PPL), Serine peptidase inhibitor, Kazal type 7 (SPINK7), EROL-like, RAN binding protein 9 (RANBP9), CD24, Keratin 6A (KRT6A), Keratin 4 (KRT4), eukaryotic translation initiation factor 3 subunit G (EIF3G), triophosphate isomerase 1 (TPL1), Cystatin-B (CSTB), deleted in malignant brain tumors 1 protein (DMBT1), *Neisseria* sp strain (B33KA_ot020_Y56, *Eikenella corrodens* and *Kingella dentriflicans* and sp clone (DE012_0t012_577_582_AD98, *Streptococcus australis* and sp clone (FN04_ot65_073_Ab83), *Fusobacterium* all species (AD99), miR-140-5p, miR-374a, miR-454, miR-15b, miR-28-5p, or miR-301a , thereby providing a first profile; effecting a therapy on the subject; analyzing a second sailva from the subject with an assay that specifically detects at least two biomarkers selected from the group consisting of Annexin 1 (ANXA1), Cystatin/Stefin B (CSTB), Semaphorin 4B (SEMA4B), S100 calcium binding protein A10 (S100A10), Periplakin (PPL), Serine peptidase inhibitor, Kazal type 7 (SPINK7), EROL-like, RAN binding protein 9 (RANBP9), CD24, Keratin 6A (KRT6A), Keratin 4 (KRT4), eukaryotic translation initiation factor 3 subunit G (EIF3G), triophosphate isomerase 1 (TPL1), Cystatin-B (CSTB), deleted in malignant brain tumors 1 protein (DMBT1), *Neisseria* sp strain (B33KA_ot020_Y56, *Eikenella corrodens* and *Kingella dentriflicans* and sp clone (DE012_0t012_577_582_AD98, *Streptococcus australis* and sp clone (FN04_ot65_073_Ab83), *Fusobacterium* all species (AD99), miR-140-5p, miR-374a, miR-454, miR-15b, miR-28-5p, or miR-301a; thereby providing a second expression profile; and comparing the first and second expression profile, thereby assessing the efficacy of a therapy.

In some embodiments, a kit is provided encompassing a solid support, wherein the solid support comprises a capture binding probe selective for at least two biomarkers selected from the group consisting of Annexin 1 (ANXA1), Cystatin/Stefin B (CSTB), Semaphorin 4B (SEMA4B), S100 calcium binding protein A10 (S100A10), Periplakin (PPL), Serine peptidase inhibitor, Kazal type 7 (SPINK7), EROL-like, RAN binding protein 9 (RANBP9), CD24, Keratin 6A (KRT6A), Keratin 4 (KRT4), eukaryotic translation initiation factor 3 subunit G (EIF3G), triophosphate isomerase 1 (TPL1), Cystatin-B (CSTB), deleted in malignant brain tumors 1 protein (DMBT1), *Neisseria* sp strain (B33KA_ot020_Y56, *Eikenella corrodens* and *Kingella dentriflicans* and sp clone (DE012_0t012_577_582_AD98, *Streptococcus australis* and sp clone (FN04_ot65_073_Ab83), *Fusobacterium* all species (AD99), miR-140-5p, miR-374a, miR-454, miR-15b, miR-28-5p, or miR-301a These and other embodiments, features and potential advantages will become apparent with reference to the following description.

DETAILED DESCRIPTION OF THE INVENTION

Introduction

Although the occurrence of new cases of gastric cancer has diminished in the recent years, gastric cancer is still one of the most common malignancies. The prognosis of gastric cancer is usually poor because it is often detected in an advanced stage.

Gastric cancer does not always show symptoms in its early stages. The late appearance of symptoms naturally delays a patient from seeking treatment. On the other hand, the clinical findings in the early stage of gastric cancer are often non-specific.

The primary diagnostic method for gastric cancer is presently gastroscopy and biopsies, and cell and aspiration cytology associated therewith. As routine gastroscopies are carried out in order to examine symptoms, such as pain in the upper abdomen or bleeding of the gastrointestinal tract, a symptomatic gastric cancer discovered in this manner is often already far advanced and thus inoperable. Attempts have also been made at improving primary diagnostics with various immunological methods, but no sufficiently specific immunological method has been successfully employed.

Described herein are methods and compositions for identifying within the general population, easily and with moderate costs, asymptomatic individuals suffering from gastric cancer in its initial stages.

Definitions

ANXA1, CSTB, SEMA4B, S100A10, PPL, SPINK7, EROL-like, RANBP9, CD24, KRT6A, KRT4, EIF3G, *Neisseria* sp strain (B33KA_ot020_Y56, *Eikenella corrodens* and *Kingella dentriflicans* and sp clone (DE012_0t012_577_582_AD98, *Streptococcus australis* and sp clone (FN04_ot65_073_Ab83) and *Fusobacterium* all species (AD99), and miR-140-5p, miR-374a, miR-454, miR-15b, miR-28-5p, and miR-301a refer to nucleic acids, e.g., gene, pre-mRNA, mRNA, and triophosphate isomerase 1 (TPL1), Cystatin-B (CSTB), and deleted in malignant brain tumors 1 protein (DMBT1) refer to polypeptides, polymorphic variants, alleles, mutants, and interspecies homologs that have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to a polypeptide encoded by a referenced nucleic acid or an amino acid sequence described herein. The nucleic acids and proteins of the invention include both naturally occurring or recombinant molecules. The nucleic acid or protein sequence is provided, for example, in SEQ ID NOs:.

"Cancer" refers to human cancers and carcinomas, sarcomas, adenocarcinomas, lymphomas, leukemias, etc., including solid and lymphoid cancers, gastric, kidney, breast, lung, kidney, bladder, colon, ovarian, prostate, pancreas, stomach, brain, head and neck, skin, uterine, testicular, esophagus, and liver cancer, including hepatocarcinoma, lymphoma, including non-Hodgkin's lymphomas (e.g., Burkitt's, Small Cell, and Large Cell lymphomas) and Hodgkin's lymphoma, leukemia, and multiple myeloma.

"Therapeutic treatment" and "cancer therapies" refers to chemotherapy, hormonal therapy, radiotherapy, and immunotherapy.

The terms "overexpress," "overexpression" or "overexpressed" interchangeably refer to a protein that is transcribed or translated at a detectably greater level, usually in a cancer cell, in comparison to a normal cell. The term includes overexpression due to transcription, post transcriptional processing, translation, post-translational processing, cellular localization (e.g, organelle, cytoplasm, nucleus, cell surface), and RNA and protein stability, as compared to a normal cell. Overexpression can be detected using conventional techniques for detecting mRNA (e.g., RT-PCR, PCR, hybridization) or proteins (e.g., ELISA, immunohistochemical techniques, mass spectroscopy). Overexpression can be 10%, 20%, 30%, 40%, 50%, 60%, 70%, 80%, 90% or more in comparison to a normal cell. In certain instances, overexpression is 1-fold, 2-fold, 3-fold, 4-fold or higher levels of transcription or translation in comparison to a normal cell.

The terms "cancer-associated antigen" or "tumor-specific marker" or "tumor marker" interchangeably refers to a molecule (typically protein or nucleic acid such as RNA) that is expressed in the cell, expressed on the surface of a cancer cell or secreted by a cancer cell in comparison to a normal cell, and which is useful for the diagnosis of cancer, for providing a prognosis, and for preferential targeting of a pharmacological agent to the cancer cell. Often, a cancer-associated antigen is overexpressed in a cancer cell in comparison to a normal cell, for instance, about 1.2-fold over expression, about 2-fold overexpression, about 3-fold overexpression or more in comparison to a normal cell. Often, a cancer-associated antigen is a cell surface molecule that is inappropriately synthesized in the cancer cell, for instance, a molecule that contains deletions, additions or mutations in comparison to the molecule expressed on a normal cell. Often, a cancer-associated antigen will be expressed exclusively on the cell surface of a cancer cell and not synthesized or expressed on the surface of a normal cell.

It will be understood by the skilled artisan that markers may be used singly or in combination with other markers for any of the uses, e.g., diagnosis or prognosis of gastric cancer, as disclosed herein.

The terms "identical" or percent "identity," in the context of two or more nucleic acids or polypeptide sequences, refer to two or more sequences or subsequences that are the same or have a specified percentage of amino acid residues or nucleotides that are the same (e.g., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site hypertext transfer protocol://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150, in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1987-2005, Wiley Interscience)).

An example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof Unless otherwise indicated, a particular nucleic acid sequence also implicitly encompasses conservatively modified variants thereof (for example, degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

A particular nucleic acid sequence also implicitly encompasses "splice variants" and nucleic acid sequences encoding truncated forms of cancer antigens. Similarly, a particular protein encoded by a nucleic acid implicitly encompasses any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5' end or at the 3' end. Polypeptides can be truncated at the N-terminal end or the C-terminal end. Truncated versions of nucleic acid or polypeptide sequences can be naturally occurring or recombinantly created.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma. -carboxyglutamate, and O-phosphoserine. Amino acid analogs refers to compounds that have the same basic chemical structure as a naturally occurring amino acid, e.g., an .alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

A "label" or a "detectable moiety" is a composition detectable by spectroscopic, photochemical, biochemical, immunochemical, chemical, or other physical means. For example, useful labels include fluorescent dyes, electron-dense reagents, enzymes (for example, as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2x SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al., supra.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C-95° C. for 30 sec-2 min., an annealing phase lasting 30 sec.–2 min., and an extension phase of about 72° C. for 1-2 min. Protocols and guidelines for low and high stringency amplification reactions are provided, e.g., in Innis et al. (1990) PCR Protocols, A Guide to Methods and Applications, Academic Press, Inc. N.Y.).

"Antibody" means a protein comprising one or more polypeptides substantially encoded by all or part of the recognized immunoglobulin genes. The recognized immunoglobulin genes, for example in humans, include the kappa (κ), lambda (λ) and heavy chain genetic loci, which together compose the myriad variable region genes, and the constant region genes mu (μ), delta (δ), gamma (γ), epsilon (ε) and alpha (α), which encode the IgM, IgD, IgG, IgE, and IgA isotypes respectively. Antibody herein is meant to include full length antibodies and antibody fragments, and may refer to a natural antibody from any organism, an engineered antibody or an antibody generated recombinantly for experimental, therapeutic or other purposes as further defined below. Antibody fragments include Fab, Fab', F(ab')$_2$, Fv, scFv or other antigen-binding subsequences of antibodies and can include those produced by the modification of whole antibodies or those synthesized de novo using recombinant DNA technologies. The term "antibody" refers to both monoclonal and polyclonal antibodies. Antibodies can be antagonists, agonists, neutralizing, inhibitory or stimulatory.

Biomarkers

Biomarkers may originate from epidemiological studies, animal studies, pathophysiological considerations and end-organ experiments. Ideally, a biomarker will have a high predictive value for a meaningful outcome measure, can be or is validated in appropriately designed prospective trials, reflects therapeutic success by corresponding changes in the surrogate marker results, and should be easy to assess in clinical practice.

Biomarkers can be used in conjunction with other diagnostic tools or used alone.

The term "surrogate marker," "biomolecular marker," "biomarker," or "marker" (also sometimes referred to herein as a "target analyte," "target species," or "target sequence") refers to a molecule whose measurement provides information as to the state of a subject. In various exemplary embodiments, the biomarker is used to assess a pathological state. Measurements of the biomarker may be used alone or combined with other data obtained regarding a subject in order to determine the state of the subject. In one embodiment, the biomarker is "differentially present" in a sample taken from a subject of one phenotypic status (e.g., having a disease) as compared with another phenotypic status (e.g., not having the disease). In one embodiment, the biomarker is "differentially present" in a sample taken from a subject undergoing no therapy or one type of therapy as compared with another type of therapy. Alternatively, the biomarker may be "differentially present" even if there is no phenotypic difference, e.g. the biomarkers may allow the detection of asymptomatic risk.

A biomarker may be over-expressed (over-abundant) or under-expressed (under abundant) relative to a control. The biomarker can be an allelic variant, truncated or mutated form of a wild-type nucleic acid or protein. The biomarker can be a splice variant.

A biomarker may be determined to be "differentially present" in a variety of ways, for example, between different phenotypic statuses if the mean or median level (particularly the expression level of the associated mRNAs as described below) of the biomarker in the different groups is calculated to be statistically significant. Common tests for statistical significance include, among others, t-test, ANOVA, Kruskal-Wallis, Wilcoxon, Mann-Whitney and odds ratio.

As described herein, a biomarker may be, for example, a small molecule, an analyte or target analyte, a nucleic acid, a protein, a metabolite or any derivative thereof or any and all combinations of these molecules, with proteins and nucleic acids finding particular use in the invention. As will be appreciated by those in the art, a large number of analytes may be detected using the present methods; basically, any biomarker for which a binding ligand, described below, may be made may be detected using the methods of the invention.

In various embodiments, the biomarkers used in the panels of the invention can be detected either as proteins or as nucleic acids (e.g. mRNA or cDNA transcripts) in any combination. In various embodiments, the protein form of a biomarker is measured. As will be appreciated by those in the art, protein assays may be done using standard techniques such as ELISA assays. In various embodiments, the nucleic acid form of a biomarker (e.g., the corresponding mRNA) is measured. In various exemplary embodiments, one or more biomarkers from a particular panel are measured using a protein assay and one or more biomarkers from the same panel are measured using a nucleic acid assay.

In some embodiments, the biomarker is a polypeptide such as TPL1, CSTB, and DMBT1.

As will be appreciated by those in the art, there are a large number of possible proteinaceous target analytes and target species that may be detected using the present invention. The term "protein," "polypeptide," or "oligopeptide" refers to at least two or more peptides or amino acids joined by one or more peptide bonds. A protein or an amino acid may be naturally or nonnaturally occurring and may be also be an analog, a derivative or a peptidomimetic structure. The term "protein" refers to wild-type sequences, variants of wild-type sequences and either of these containing analogs or derivatized amino acids. In various embodiments, variants of the sequences described herein, including proteins and nucleic acids based on e.g. splice variants, variants comprising a deletion, addition, substitution, fragments, preproprotein, processed preproprotein (e.g. without a signaling peptide), processed proprotein (e.g. resulting in an active form), nonhuman sequences and variant nonhuman sequences may be used as biomarkers.

In various embodiments, the biomarker is a nucleic acid. The term "nucleic acid" or "oligonucleotide" or grammatical equivalents herein means at least two nucleotides covalently linked together. A nucleic acid of the present invention will generally contain phosphodiester bonds, although in some cases, as outlined below, for example in the use of binding ligand probes, nucleic acid analogs are included that may have alternate backbones.

Biomarkers can also be bacterial nucleic acids or proteins. Over 700 species of bacteria have been identified to exist within the mouth. The presence, absence, or level of 16S rRNA from bacteria in a sample may correlate with a disease or condition. "Bacteria" refers to small prokaryotic organisms (linear dimensions of around 1 µm) with non-compartmentalized circular DNA and ribosomes of about 70 S. "16S RNA" refers to a nucleic acid component of the 30S subunit of prokaryotic ribosomes; the gene that encodes the 16S rRNA or the 16S rRNA itself Bacterial strains of species or phylotypes have less than about a 2% difference in 16S rRNA. Closely related species or phylotypes generally have between about a 2% and about a 4% difference in 16S rRNA, whereas a genus often has between about a 5% and about a 10% difference in 16S rRNA.

To resolve the identity of bacerial populations, probes on a microarray can be designed, for example, to take advantage of conserved features of the 16S rRNA gene. For example, probes complementary to the more conserved features regions identify species in a large phylogenetic group, each group corresponding to a higher taxon (for example, domain, phylum, class, order, or family). Probes complementary to more variable regions distinguish genera and species.

Biomarkers can also include micro RNAs. "MicroRNAs" (miRs) refers to a class of small naturally occurring non-coding RNAs (18-24 nucleotides) that regulate gene expression. Many microRNAs are well conserved across species and they are present in a broad range of species: plants, nematodes, fruit flies and humans. MicroRNAs have partially or perfect complementary sequence to one or more messenger RNA molecules (mRNAs) and their main function is to negatively regulate the expression of genes. In particular, microRNAs bind to the 3' untranslated regions of mRNAs (3-UTR) thus leading to down regulation of mRNAs in a variety of ways such as mRNA cleavage, translational repression and deadenylation.

A variety of experimental approaches and different techniques have been used to identify new microRNAs, as well as to study their expression pattern in the different biological processes. The cloning and identification of new microRNAs have been successfully accomplished from size fractioned RNA samples using small RNA cloning approaches.

One of the first techniques used for detection and profiling of microRNAs was Northern Blotting, where hybridization is done with a complementary $^{32}$P, digoxigenin-labeled oligo or modified Locked-nucleic-acid (LNA) oligonucleotides after gel separation.

Other techniques that have been developed to specifically detect microRNAs are a modified invader assay (a synthetic oligonucleotide, the probe, which is in an appropriate overlap-flap structure is enzymatically cleavage by a structure-specific 5* nuclease) and in situ hybridization (using fluorescent-labeled complementary probes containing chemically modified nucleotides e.g. LNAs). Another widely used technique for detection and profiling of microRNAs is the use of oligonucleotide micro-array based detection platforms either with DNA capture probes or using modified Locked-nucleic-acid (LNA) oligonucleotides in which the ribose moiety is modified with an extra bridge that connects the 2'-0 and 4'-C atoms.

In addition, quantitative real-time PCR (reverse transcriptase/ polymerase chain reaction using Taqman or SYBR green technology) has been used for detection and profiling of precursor or mature microRNAs. This technique is sensitive and requires low amounts of starting material for the detection of individual mature microRNAs. Taqman microRNA arrays have been developed that provide the sensitivity of the qRT-PCR, while at the same time enables the simultaneously detection of different microRNAs in one sample.

Biomarker Panels

Any combination of the biomarkers described herein is used to assemble a biomarker panel, which is detected or measured as described herein. As is generally understood in the art, a combination may refer to an entire set or any subset or subcombination thereof. The term "biomarker panel," "biomarker profile," or "biomarker fingerprint" refers to a set of biomarkers. As used herein, these terms can also refer to any form of the biomarker that is measured. Thus, if cystatin B is part of a biomarker panel, then either cystatin B mRNA, for example, could be considered to be part of the panel. While individual biomarkers are useful as diagnostics, combination of biomarkers can sometimes provide greater value in determining a particular status than single biomarkers alone. Specifically, the detection of a plurality of biomarkers in a sample can increase the sensitivity and/or specificity of the test. Thus, in various embodiments, a biomarker panel may include 1, 2, 3, 4, 5, 6, 7, 8, 9, 10, 11, 12, 13, 14, 15, 16, 17, 18, 19, 20, 21, 22, 23, 24, 25, or more biomarkers. In various exemplary embodiments, the biomarker panel consists of a minimum number of biomarkers to generate a maximum amount of information. Thus, in various embodiments, the biomarker panel consists of 2, 3, 4, 5, 6, 7, 8, 9, 10, 11, 12, 13, 14, 15, 16, 17, 18, 19, 20, 21, 22, 23, 24, 25 or more biomarkers. Where a biomarker panel "consists of" a set of biomarkers, no biomarkers other than those of the set are present. In exemplary embodiments, the biomarker panel consists of 2 biomarkers disclosed herein. In various embodiments, the biomarker panel consists of 3 biomarkers disclosed herein. In various embodiments, the biomarker panel consists of 4 biomarkers disclosed herein. In various embodiments, the biomarker panel consists of 5 biomarkers disclosed herein. In exemplary embodiments, the biomarker panel consists of 6 biomarkers disclosed herein. In various embodiments, the biomarker panel consists of 7 biomarkers disclosed herein. In various embodiments, the biomarker panel consists of 8 biomarkers disclosed herein. In various embodiments, the biomarker panel consists of 9 biomarkers disclosed herein. In various embodiments, the biomarker panel consists of 10 biomarkers disclosed herein. In various embodiments, the biomarker panel consists of 11 biomarkers disclosed herein. In various embodiments, the biomarker panel consists of 12 biomarkers disclosed herein. In various embodiments, the biomarker panel consists of 13 biomarkers disclosed herein. In various embodiments, the biomarker panel consists of 14 biomarkers disclosed herein. In various embodiments, the biomarker panel consists of 15 biomarkers disclosed herein. In various embodiments, the biomarker panel consists of 16 biomarkers disclosed herein. In various embodiments, the biomarker panel consists of 17 biomarkers disclosed herein. In various embodiments, the biomarker panel consists of 18 biomarkers disclosed herein. In various embodiments, the biomarker panel consists of 19 biomarkers disclosed herein. In various embodiments, the biomarker panel consists of 20 biomarkers disclosed herein. In various embodiments, the biomarker panel consists of 21 biomarkers disclosed herein. In various embodiments, the biomarker panel consists of 22 biomarkers disclosed herein. In various embodiments, the biomarker panel consists of 23 biomarkers disclosed herein. In various embodiments, the biomarker panel consists of 24 biomarkers disclosed herein. In various embodiments, the biomarker panel consists of 25 biomarkers disclosed herein.

Furthermore the biomarker panel can be a combination of two, three, or four biomarker types wherein the biomarker types comprise mRNA, a polypeptide, a bacterial marker and/or a micro-RNA marker. In some instances the biomarker panel is a combination of at least one mRNA biomarker and at least one polypeptide biomarker. In some instances the biomarker panel is a combination of at least one mRNA biomarker and at least one bacterial marker. In some instances the biomarker panel is a combination of at least one mRNA biomarker and at least one micro-RNA marker. In some instances the biomarker panel is a combination of at least one polypeptide biomarker and at least one bacterial marker. In some instances the biomarker panel is a combination of at least one polypeptide biomarker and at least one micro-RNA marker. In some instances the biomarker panel is a combination of at least one bacterial marker and at least one micro-RNA marker.

In some instances the biomarker panel can be a combination of three biomarker types. Thus, in some instances the biomarker panel is a combination of at least one mRNA biomarker, at least one polypeptide biomarker, and at least one bacterial marker. In some instances the biomarker panel is a combination of at least one mRNA biomarker, at least one polypeptide biomarker, and at least one micro-RNA marker. In some instances the biomarker panel is a combination of at least one polypeptide biomarker, at least one bacterial marker and at least one micro-RNA marker.

In some instances the mRNA biomarkers include Annexin 1 (ANXA1), Cystatin/Stefin B (CSTB), Semaphorin 4B (SEMA4B), S100 calcium binding protein A10 (S100A10), Periplakin (PPL), Serine peptidase inhibitor, Kazal type 7 (SPINK7), EROL-like, RAN binding protein 9 (RANBP9), CD24, Keratin 6A (KRT6A), Keratin 4 (KRT4), but not eukaryotic translation initiation factor 3 subunit G (EIF3G). In some instances the mRNA biomarkers include Annexin 1 (ANXA1), Cystatin/Stefin B (CSTB), Semaphorin 4B (SEMA4B), S100 calcium binding protein A10 (S100A10), Periplakin (PPL), Serine peptidase inhibitor, Kazal type 7 (SPINK7), EROL-like, RAN binding protein 9 (RANBP9), CD24, Keratin 6A (KRT6A), eukaryotic translation initiation factor 3 subunit G (EIF3G), but not Keratin 4 (KRT4). In some instances the mRNA biomarkers include Annexin 1 (ANXA1), Cystatin/Stefin B (CSTB), Semaphorin 4B (SEMA4B), S100 calcium binding protein A10 (S100A10), Periplakin (PPL), Serine peptidase inhibitor, Kazal type 7 (SPINK7), EROL-like, RAN binding protein 9 (RANBP9), CD24, Keratin 4 (KRT4), eukaryotic translation initiation factor 3 subunit G (EIF3G), but not Keratin 6A (KRT6A). In some instances the mRNA biomarkers include Annexin 1 (ANXA1), Cystatin/Stefin B (CSTB), Semaphorin 4B (SEMA4B), S100 calcium binding protein A10 (S100A10), Periplakin (PPL), Serine peptidase inhibitor, Kazal type 7 (SPINK7), EROL-like, RAN binding protein 9 (RANBP9), but not CD24, Keratin 6A (KRT6A), Keratin 4 (KRT4), eukaryotic translation initiation factor 3 subunit G (EIF3G) but not KRT4. In some instances the mRNA biomarkers include Annexin 1 (ANXA1), Cystatin/Stefin B (CSTB), Semaphorin 4B (SEMA4B), S100 calcium binding protein A10 (S100A10), Periplakin (PPL), Serine peptidase inhibitor, Kazal type 7 (SPINK7), EROL-like, CD24, Keratin 6A (KRT6A), Keratin 4 (KRT4), eukaryotic translation initiation factor 3 subunit G (EIF3G), but not RAN binding protein 9 (RANBP9). In some instances the mRNA biomarkers include Annexin 1 (ANXA1), Cystatin/Stefin B (CSTB), Semaphorin 4B (SEMA4B), S100 calcium binding protein A10 (S100A10), Periplakin (PPL), Serine peptidase inhibitor, Kazal type 7 (SPINK7), RAN binding protein 9 (RANBP9), CD24, Keratin 6A (KRT6A), Keratin 4 (KRT4), eukaryotic translation initiation factor 3 subunit G (EIF3G), but not EROL-like. In some instances the mRNA biomarkers include Annexin 1 (ANXA1), Cystatin/Stefin B (CSTB), Semaphorin 4B (SEMA4B), S100 calcium binding protein A10 (S100A10), Periplakin (PPL), Serine peptidase inhibitor, EROL-like, RAN binding protein 9 (RANBP9), CD24, Keratin 6A (KRT6A), Keratin 4 (KRT4), eukaryotic translation initiation factor 3 subunit G (EIF3G), but not Kazal type 7 (SPINK7). In some instances the mRNA biomarkers include Annexin 1 (ANXA1), Cystatin/Stefin B (CSTB), Semaphorin 4B (SEMA4B), S100 calcium binding protein A10 (S100A10), Periplakin (PPL), but not Serine peptidase inhibitor, Kazal type 7 (SPINK7), EROL-like, RAN binding protein 9 (RANBP9), CD24, Keratin 6A (KRT6A), Keratin 4 (KRT4), eukaryotic translation initiation factor 3 subunit G (EIF3G), but not Serine peptidase inhibitor. In some instances the mRNA biomarkers include Annexin 1 (ANXA1), Cystatin/Stefin B (CSTB), Semaphorin 4B (SEMA4B), S100 calcium binding protein A10 (S100A10), but not Periplakin (PPL), Serine peptidase inhibitor, Kazal type 7 (SPINK7), EROL-like, RAN binding protein 9 (RANBP9), CD24, Keratin 6A (KRT6A), Keratin 4 (KRT4), eukaryotic translation initiation factor 3 subunit G (EIF3G), but not Periplakin (PPL). In some instances the mRNA biomarkers include Annexin 1 (ANXA1), Cystatin/Stefin B (CSTB), Semaphorin 4B (SEMA4B), but not S100 calcium binding protein A10 (S100A10), Periplakin (PPL), Serine peptidase inhibitor, Kazal type 7 (SPINK7), EROL-like, RAN binding protein 9 (RANBP9), CD24, Keratin 6A (KRT6A), Keratin 4 (KRT4), eukaryotic translation initiation factor 3 subunit G (EIF3G), but not S100 calcium binding protein A10 (S100A10). In some instances the mRNA biomarkers include Annexin 1 (ANXA1), Cystatin/Stefin B (CSTB), S100 calcium binding protein A10 (S100A10), Periplakin (PPL), Serine peptidase inhibitor, Kazal type 7 (SPINK7), EROL-like, RAN binding protein 9 (RANBP9), CD24, Keratin 6A (KRT6A), Keratin 4 (KRT4), eukaryotic translation initiation factor 3 subunit G (EIF3G), but not Semaphorin 4B (SEMA4B). In some instances the mRNA biomarkers include Annexin 1 (ANXA1), Semaphorin 4B (SEMA4B), S100 calcium binding protein A10 (S100A10), Periplakin (PPL), Serine peptidase inhibitor, Kazal type 7 (SPINK7), EROL-like, RAN binding protein 9 (RANBP9), CD24, Keratin 6A (KRT6A), Keratin 4 (KRT4), eukaryotic translation initiation factor 3 subunit G (EIF3G), but not Cystatin/Stefin B (CSTB). In some instances the mRNA biomarkers include Cystatin/Stefin B (CSTB), Semaphorin 4B (SEMA4B), S100 calcium binding protein A10 (S100A10), Periplakin (PPL), Serine peptidase inhibitor, Kazal type 7 (SPINK7), EROL-like, RAN binding protein 9 (RANBP9), CD24, Keratin 6A (KRT6A), Keratin 4 (KRT4), eukaryotic translation initiation factor 3 subunit G (EIF3G) but not Annexin 1 (ANXA1). In some instances the mRNA biomarkers include Cystatin/Stefin B (CSTB), Semaphorin 4B (SEMA4B), S100 calcium binding protein A10 (S100A10), Periplakin (PPL), Serine peptidase inhibitor, Kazal type 7 (SPINK7), EROL-like, RAN binding protein 9 (RANBP9), CD24, Keratin 6A (KRT6A), Keratin 4 (KRT4), eukaryotic translation initiation factor 3 subunit G (EIF3G), Annexin 1 (ANXA1), but not CD24.

In some instances the polypeptide biomarkers include TPL1, CSTB, but not DMBT1. In some instances the polypeptide biomarkers include TPL1, DMBT1, but not CSTB. In some instances the polypeptide biomarkers include DMBT1 and CSTB but not TPL1.

In some instances the bacterial marker includes *Neisseria* sp strain (B33KA_ot020_Y56, *Eikenella corrodens* and *Kingella dentriflicans* and sp clone (DE012_0t012_577_582_AD98, *Streptococcus australis* and sp clone (FN04_ot65_073_Ab83) but not *Fusobacterium* all species (AD99). In some instances the bacterial marker includes *Neisseria* sp strain (B33KA_ot020_Y56, *Eikenella corrodens* and *Kingella dentriflicans* and sp clone (DE012_0t012_577_582_AD98, *Fusobacterium* all species (AD99) but not *Streptococcus australis* and sp clone (FN04_ot65_073_Ab83). In some instances the bacterial marker includes *Neisseria* sp strain (B33KA_ot020_Y56), *Eikenella corrodens* and *Kingella dentriflicans* and sp clone (DE012 _0t012_577_582_AD98), *Streptococcus australis* and sp clone (FN04_ot65_073_Ab83), *Fusobacterium* all species (AD99) but not .*Eikenella corrodens* and *Kingella dentriflicans* and sp clone (DE012_0t012_577_582_AD98). In some instances the bacterial marker includes *Eikenella corrodens* and *Kingella dentriflicans* and sp clone (DE012_0t012_577_582_AD98), *Streptococcus australis* and sp clone (FN04_ot65_073_Ab83), *Fusobacterium* all species (AD99), *Eikenella corrodens* and *Kingella dentriflicans* and sp clone (DE012_0t012_577_582_AD98), but not *Neisseria* sp strain (B33KA_ot020_Y56).

In some instances the micro-RNA marker includes miR-140-5p, miR-374a, miR-454, miR-15b, miR-28-5p, but not miR-301a. In some instances the micro-RNA marker includes miR-140-5p, miR-374a, miR-454, miR-15b, miR-301a, but not miR-28-5p. In some instances the micro-RNA marker includes miR-140-5p, miR-374a, miR-454, miR-301a, miR-28-5p, but not miR-15b. In some instances the micro-RNA marker includes miR-140-5p, miR-374a, miR-454, miR-15b, miR-301a, miR-28-5p, but not miR-454. In some instances the micro-RNA marker includes miR-140-5p, miR-374a, miR-454, miR-15b, miR-28-5p, miR-374a, but not miR-301a. In some instances the micro-RNA marker includes miR-374a, miR-454, miR-15b, miR-28-5p, miR-374a, miR-301a, but not miR-140-5p.

A biomarker can also be a clinical parameter. The term "clinical parameter" refers to all non-sample or non-analyte biomarkers of subject health status or other characteristics, such as, without limitation, age, ethnicity, gender, family history, height, and weight.

The biomarkers of the invention show a statistically significant difference in gastric cancer diagnosis. In various embodiments, diagnostic tests that use these biomarkers alone or in combination show a sensitivity and specificity of at least about 85%, at least about 90%, at least about 95%, at least about 98% and about 100%.

Measurement and Detection of Biomarkers

Biomarkers generally can be measured and detected through a variety of assays, methods and detection systems known to one of skill in the art. The term "measuring," "detecting," or "taking a measurement" refers to a quantitative or qualitative determination of a property of an entity, for example, quantifying the amount or concentration of a molecule or the activity level of a molecule. The term "concentration" or "level" can refer to an absolute or relative quantity. Measuring a molecule may also include determining the absence or presence of the molecule. Various methods include but are not limited to refractive index spectroscopy (RI), ultra-violet spectroscopy (UV), fluorescence analysis, electrochemical analysis, radiochemical analysis, near-infrared spectroscopy (near-IR), infrared (IR) spectroscopy, nuclear magnetic resonance spectroscopy (NMR), light scattering analysis (LS), mass spectrometry, pyrolysis mass spectrometry, nephelometry, dispersive Raman spectroscopy, gas chromatography, liquid chromatography, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, colorimetry and surface plasmon resonance (such as according to systems provided by Biacore Life Sciences). See also PCT Publications WO/2004/056456 and WO/2004/088309. In this regard, biomarkers can be measured using the above-mentioned detection methods, or other methods known to the skilled artisan. Other biomarkers can be similarly detected using reagents that are specifically designed or tailored to detect them.

Different types of biomarkers and their measurements can be combined in the compositions and methods of the present invention. In various embodiments, the protein form of the biomarkers is measured. In various embodiments, the nucleic acid form of the biomarkers is measured. In exemplary embodiments, the nucleic acid form is mRNA. In various embodiments, measurements of protein biomarkers are used in conjunction with measurements of nucleic acid biomarkers.

Methods for detecting mRNA, such as RT-PCR, real time PCR, branch DNA, NASBA and others, are well known in the art. Using sequence information provided by the database entries for the biomarker sequences, expression of the biomarker sequences can be detected (if present) and measured using techniques well known to one of ordinary skill in the art. For example, sequences in sequence database entries or sequences disclosed herein can be used to construct probes for detecting biomarker RNA sequences in, e.g., Northern blot hybridization analyses or methods which specifically, and, preferably, quantitatively amplify specific nucleic acid sequences. As another example, the sequences can be used to construct primers for specifically amplifying the biomarker sequences in, e.g., amplification-based detection methods such as reverse-transcription based polymerase chain reaction (RT-PCR). When alterations in gene expression are associated with gene amplification, deletion, polymorphisms and mutations, sequence comparisons in test and reference populations can be made by comparing relative amounts of the examined DNA sequences in the test and reference cell populations. In addition to Northern blot and RT-PCR, RNA can also be measured using, for example, other target amplification methods (e.g., TMA, SDA, NASBA), signal amplification methods (e.g., bDNA), nuclease protection assays, in situ hybridization and the like.

In one embodiment in the present invention are biochip assays. By "biochip" or "chip" herein is meant a composition generally comprising a solid support or substrate to which a capture binding ligand (also called an adsorbent, affinity reagent or binding ligand, or when nucleic acid is measured, a capture probe) is attached and can bind either proteins, nucleic acids or both. Generally, where a biochip is used for measurements of protein and nucleic acid biomarkers, the protein biomarkers are measured on a chip separate from that used to measure the nucleic acid biomarkers. For nonlimiting examples of additional platforms and methods useful for measuring nucleic acids, see Publications US/2006/0275782, US/2005/0064469 and DE10201463. In various embodiments, biomarkers are measured on the same platform, such as on one chip. In various embodiments, biomarkers are measured using different platforms and/or different experimental runs.

By "binding ligand," "capture binding ligand," "capture binding species," "capture probe" or grammatical equivalents herein is meant a compound that is used to detect the presence of or to quantify, relatively or absolutely, a target analyte, target species or target sequence (all used interchangeably) and that will bind to the target analyte, target species or target sequence. Generally, the capture binding ligand or capture probe allows the attachment of a target species or target sequence to a solid support for the purposes of detection as further described herein. Attachment of the target species to the capture binding ligand may be direct or indirect. In exemplary embodiments, the target species is a biomarker. As will be appreciated by those in the art, the composition of the binding ligand will depend on the composition of the biomarker. Binding ligands for a wide variety of biomarkers are known or can be readily found using known techniques. For example, when the biomarker is a protein, the binding ligands include proteins (particularly including antibodies or fragments thereof ($F_{ab}$s, etc.) as discussed further below) or small molecules. The binding ligand may also have cross-reactivity with proteins of other species. Antigen-antibody pairs, receptor-ligands, and carbohydrates and their binding partners are also suitable analyte-binding ligand pairs. In various embodiments, the binding ligand may be nucleic acid. Nucleic acid binding ligands find particular use when proteins are the targets; alternatively, as is generally described in U.S. Pat. Nos. 5,270,163; 5,475,096; 5,567,588; 5,595,877; 5,637,459; 5,683,867; 5,705,337 and related patents, hereby incorporated by reference, nucleic acid "aptamers" can be developed for binding to virtually any biomarker. Nucleic acid binding ligands also find particular use when nucleic acids are binding targets. There is a wide body of literature relating to the development of binding partners based on combinatorial chemistry methods. In these embodiments, when the binding ligand is a nucleic acid, preferred compositions and techniques are outlined in PCT Publication WO/1998/020162, hereby incorporated by reference.

In various exemplary embodiments, the capture binding ligand is an antibody. These embodiments are particularly useful for the detection of the protein form of a biomarker.

Detecting or measuring the level (e.g. the transcription level) of a biomarker involves binding of the biomarker to a capture binding ligand, generally referred to herein as a "capture probe" when the mRNA of the biomarker is to be detected on a solid support. In that sense, the biomarker is a target sequence. The term "target sequence" or "target nucleic acid" or grammatical equivalents herein means a nucleic acid sequence that may be a portion of a gene, a regulatory sequence, genomic DNA, cDNA, RNA including mRNA and rRNA, or others. As is outlined herein, the target sequence may be a target sequence from a sample, or a secondary target such as a product of an amplification reaction such as PCR etc. In some embodiments, measuring a nucleic acid can thus refer to measuring the complement of the nucleic acid. It may be any length, with the understanding that longer sequences are more specific.

The target sequence may also comprise different target domains; for example, a first target domain of the sample target sequence may hybridize to a first capture probe, a second target domain may hybridize to a label probe (e.g. a "sandwich assay" format), etc. The target domains may be adjacent or separated as indicated. Unless specified, the terms "first" and "second" are not meant to confer an orientation of the sequences with respect to the 5'-3' orientation of the target sequence. For example, assuming a 5'-3' orientation of the target sequence, the first target domain may be located either 5' to the second domain, or 3' to the second domain.

When nucleic acids are used as the target analyte, the assays of the invention can take on a number of embodiments. In one embodiment, the assays are done in solution format, using any number of solution based formats. In one embodiment, end-point or real time PCR formats are used, as are well known in the art. These assays can be done either as a panel, in individual tubes or wells, or as multiplex assays, using sets of primers and different labels within a single tube or well. In addition to PCR-based solution formats, other formats can be utilized, including, but not limited to for example ligation based assays utilizing FRET dye pairs. In this embodiment, only upon ligation of two (or more) probes hybridized to the target sequence is a signal generated.

In many embodiments, the assays are done on a solid support, utilizing a capture probe associated with the surface. As discussed herein, the capture probes (or capture binding ligands, as they are sometimes referred to) can be covalently attached to the surface, for example using capture probes terminally modified with functional groups, for example amino groups, that are attached to modified surfaces such as silanized glass. Alternatively, non-covalent attachment, such as electrostatic, hydrophobic/hydrophilic adhesion can be utilized. As is appreciated by those in the art and discussed herein, a large number of attachments are possible on a wide variety of surfaces.

In this embodiment, the assays can take on a number of formats. In one embodiment, the target sequence comprises a detectable label, as described herein. In this embodiment, the label is generally added to the target sequence during amplification of the target in one of two ways: either labeled primers are utilized during the amplification step or labeled dNTPs are used, both of which are well known in the art. The label can either be a primary or secondary label as discussed herein. For example, in one embodiment, the label on the primer and/or a dNTP is a primary label such as a fluorophore. Alternatively, the label may be a secondary label such as biotin or an enzyme; for example, in one embodiment, the primers or dNTPs are labeled with biotin, and then a streptavidin/label complex is added. In one embodiment, the streptavidin/label complex contains a label such as a fluorophore. In an alternative embodiment, the streptavidin/label complex comprises an enzymatic label. For example, the complex can comprise horseradish peroxidase, and upon addition of TMB, the action of the horseradish peroxidase causes the TMB to precipitate, causing an optically detectable event. This has a particular benefit in that the optics for detection does not require the use of a fluorimeter.

In alternate embodiments, the solid phase assay relies on the use of a labeled soluble capture ligand, sometimes referred to as a "label probe" or "signaling probe" when the target analyte is a nucleic acid. In this format, the assay is a "sandwich" type assay, where the capture probe binds to a first domain of the target sequence and the label probe binds to a second domain. In this embodiment, the label probe can also be either a primary (e.g. a fluorophore) or a secondary (biotin or enzyme) label. In one embodiment, the label probe comprises biotin, and a streptavidin/enzyme complex is used, as discussed herein. As above, for example, the complex can comprise horseradish peroxidase, and upon addition of TMB, the action of the horseradish peroxidase causes the TMB to precipitate, causing an optically detectable event.

Detection of a target species in some embodiments requires a "label" or "detectable marker" (as described below) that can be incorporated in a variety of ways. Thus, in various embodiments, the composition comprises a "label" or a "detectable marker." In one embodiment, the target species (or target analyte or target sequence) is labeled; binding of the target species thus provides the label at the surface of the solid support.

In embodiments finding particular use herein, a sandwich format is utilized, in which target species are unlabeled. In these embodiments, a "capture" or "anchor" binding ligand is attached to the detection surface as described herein, and a soluble binding ligand (frequently referred to herein as a "signaling probe," "label probe" or "soluble capture ligand") binds independently to the target species and either directly or indirectly comprises at least one label or detectable marker.

By "label" or "labeled" herein is meant that a compound has at least one molecule, element, isotope or chemical compound attached to enable the detection of the compound. In general, labels fall into four classes: a) isotopic labels, which may be radioactive or heavy isotopes; b) magnetic, electrical, thermal; c) colored or luminescent dyes; and d) enzymes; although labels include particles such as magnetic particles as well. The dyes may be chromophores or phosphors but are preferably fluorescent dyes, which due to their strong signals provide a good signal-to-noise ratio for decoding. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue, Texas Red, Alexa dyes and others described in the 6th Edition of the Molecular Probes Handbook by Richard P. Haugland, hereby expressly incorporated by reference. Additional labels include nanocrystals or Q-dots as described in U.S. Pat. No. 6,544,732 incorporated by reference.

In various embodiments, a secondary detectable label is used. A secondary label is one that is indirectly detected; for example, a secondary label can bind or react with a primary label for detection, can act on an additional product to generate a primary label (e.g. enzymes), or may allow the separation of the compound comprising the secondary label from unlabeled materials, etc. Secondary labels include, but are not limited to, one of a binding partner pair; chemically modifiable moieties; nuclease inhibitors, enzymes such as horseradish peroxidase, alkaline phosphatases, luciferases, etc. Secondary labels can also include additional labels.

In various embodiments, the secondary label is a binding partner pair. For example, the label may be a hapten or antigen, which will bind its binding partner. For example, suitable binding partner pairs include, but are not limited to: antigens (such as proteins (including peptides)) and antibodies (including fragments thereof ($F_{ab}$s, etc.)); proteins and small molecules, including biotin/streptavidin; enzymes and substrates or inhibitors; other protein-protein interacting pairs; receptor-ligands; and carbohydrates and their binding partners. Nucleic acid—nucleic acid binding proteins pairs are also useful. In general, the smaller of the pair is attached to the NTP for incorporation into the primer. Preferred binding partner pairs include, but are not limited to, biotin (or imino-biotin) and streptavidin, digeoxinin and Abs, and Prolinx™ reagents.

In the sandwich formats of the invention, an enzyme serves as the secondary label, bound to the soluble capture ligand. Of particular use in some embodiments is the use of horseradish peroxidase, which when combined with 3,3',5,5'-tetramethylbenzidine (TMB) forms a colored precipitate which is then detected. In some cases, the soluble capture ligand comprises biotin, which is then bound to an enzyme-streptavidin complex and forms a colored precipitate with the addition of TMB.

In various embodiments, the label or detectable marker is a conjugated enzyme (for example, horseradish peroxidase). In various embodiments, the system relies on detecting the precipitation of a reaction product or on a change in, for example, electronic properties for detection. In various embodiments, none of the compounds comprises a label.

As used herein, the term "fluorescent signal generating moiety" or "fluorophore" refers to a molecule or part of a molecule that absorbs energy at one wavelength and re-emits energy at another wavelength. Fluorescent properties that can be measured include fluorescence intensity, fluorescence lifetime, emission spectrum characteristics, energy transfer, and the like.

Signals from single molecules can be generated and detected by a number of detection systems, including, but not limited to, scanning electron microscopy, near field scanning optical microscopy (NSOM), total internal reflection fluorescence microscopy (TIRFM), and the like. Abundant guidance is found in the literature for applying such techniques for analyzing and detecting nanoscale structures on surfaces, as evidenced by the following references that are incorporated by reference: Reimer et al, editors, *Scanning Electron Microscopy: Physics of Image Formation and Microanalysis*, 2nd Edition (Springer, 1998); Nie et al, *Anal. Chem.*, 78: 1528-1534 (2006); Hecht et al, *Journal Chemical Physics*, 112: 7761-7774 (2000); Zhu et al, editors, *Near-Field Optics: Principles and Applications* (World Scientific Publishing, Singapore, 1999); Drmanac, PCT Publication WO/2004/076683; Lehr et al, *Anal. Chem.*, 75: 2414-2420 (2003); Neuschafer et al, *Biosensors & Bioelectronics*, 18: 489-497 (2003); Neuschafer et al, U.S. Pat. No. 6,289,144; and the like.

Thus, a detection system for fluorophores includes any device that can be used to measure fluorescent properties as discussed above. In various embodiments, the detection system comprises an excitation source, a fluorophore, a wavelength filter to isolate emission photons from excitation photons and a detector that registers emission photons and produces a recordable output, in some embodiments as an electrical signal or a photographic image. Examples of detection devices include without limitation spectrofluorometers and microplate readers, fluorescence microscopes, fluorescence scanners (including e.g. microarray readers) and flow cytometers.

In various exemplary embodiments, the binding of the biomarker to the binding ligand is specific or selective, and the binding ligand is part of a binding pair. By "specifically bind" or "selectively bind" or "selective for" a biomarker herein is meant that the ligand binds the biomarker with specificity sufficient to differentiate between the biomarker and other components or contaminants of the test sample.

The term "solid support" or "substrate" refers to any material that can be modified to contain discrete individual sites appropriate for the attachment or association of a capture binding ligand. Suitable substrates include metal surfaces such as gold, electrodes, glass and modified or functionalized glass, plastics (including acrylics, polystyrene and copolymers of styrene and other materials, polypropylene, polyethylene, polybutylene, polycarbonate, polyurethanes, Teflon, derivatives thereof, etc.), polysaccharides, nylon or nitrocellulose, resins, mica, silica or silica-based materials including silicon and modified silicon, carbon, metals, inorganic glasses, fiberglass, ceramics, GETEK (a blend of polypropylene oxide and fiberglass) and a variety of other polymers. Of particular use in the present invention are the ClonDiag materials described below.

Frequently, the surface of a biochip comprises a plurality of addressable locations, each of which comprises a capture binding ligand. An "array location," "addressable location," "pad" or "site" herein means a location on the substrate that comprises a covalently attached capture binding ligand. An "array" herein means a plurality of capture binding ligands in a regular, ordered format, such as a matrix. The size of the array will depend on the composition and end use of the array. Arrays containing from about two or more different capture binding ligands to many thousands can be made. Generally, the array will comprise 3, 4, 5, 6, 7 or more types of capture binding ligands depending on the end use of the array. In the present invention, the array can include controls, replicates of the markers and the like. Exemplary ranges are from about 3 to about 50. In some embodiments, the compositions of the invention may not be in array format; that is, for some embodiments, compositions comprising a single capture ligand may be made as well. In addition, in some arrays, multiple substrates may be used, either of different or identical compositions. Thus for example, large arrays may comprise a plurality of smaller substrates.

Accordingly, in one aspect, the invention provides a composition comprising a solid support comprising a capture binding ligand for each biomarker of a biomarker panel. In various embodiments, the capture ligand is a nucleic acid. In various embodiments, the capture binding ligand is an antibody. In various embodiments, the composition further comprises a soluble binding ligand for each biomarker of a biomarker panel.

A number of different biochip array platforms as known in the art may be used. For example, the compositions and methods of the present invention can be implemented with array platforms such as GeneChip® (Affymetrix), CodeLink™ Bioarray (Amersham), Expression Array System (Applied Biosystems), SurePrint microarrays (Agilent), Sentrix® LD BeadChip or Sentrix® Array Matrix (Illumina) and Verigene (Nanosphere).

In various exemplary embodiments, detection and measurement of biomarkers utilizes colorimetric methods and systems in order to provide an indication of binding of a target analyte or target species. In colorimetric methods, the presence of a bound target species such as a biomarker will result in a change in the absorbance or transmission of light by a sample or substrate at one or more wavelengths. Detection of the absorbance or transmission of light at such wavelengths thus provides an indication of the presence of the target species.

A detection system for colorimetric methods includes any device that can be used to measure colorimetric properties as discussed above. Generally, the device is a spectrophotometer, a colorimeter or any device that measures absorbance or transmission of light at one or more wavelengths. In various embodiments, the detection system comprises a light source; a wavelength filter or monochromator; a sample container such as a cuvette or a reaction vial; a detector, such as a photoresistor, that registers transmitted light; and a display or imaging element.

In various exemplary embodiments, a ClonDiag chip platform is used for the colorimetric detection of biomarkers. In various embodiments, a ClonDiag ArrayTube (AT) is used. One unique feature of the ArrayTube is the combination of a micro probe array (the biochip) and micro reaction vial. In various embodiments, where a target sequence is a nucleic acid, detection of the target sequence is done by amplifying and biotinylating the target sequence contained in a sample and optionally digesting the amplification products. The amplification product is then allowed to hybridize with probes contained on the ClonDiag chip. A solution of a streptavidin-enzyme conjugate, such as Poly horseradish peroxidase (HRP) conjugate solution, is contacted with the ClonDiag chip. After washing, a dye solution such as o-dianisidine substrate solution is contacted with the chip. Oxidation of the dye results in precipitation that can be detected colorimetrically. Further description of the ClonDiag platform is found in Monecke S, Slickers P, Hotzel H et al., *Clin Microbiol Infect* 2006, 12: 718-728; Monecke S, Berger-Bächi B, Coombs C et al., *Clin Microbiol Infect*

2007, 13: 236-249; Monecke S, Leube I and Ehricht R, *Genome Lett* 2003, 2: 106-118; Monecke S and Ehricht R, *Clin Microbiol Infect* 2005, 11: 825-833; German Patent DE 10201463; US Publication US/2005/0064469 and ClonDiag, *ArrayTube (AT) Experiment Guideline for DNA-Based Applications*, version 1.2, 2007, all incorporated by reference in their entirety. One of skill in the art will appreciate that numerous other dyes that react with a peroxidase can be utilized to produce a colorimetric change, such as 3,3',5,5'-tetramethylbenzidine (TMB). For information on specific assay protocols, see www.clondiag.com/technologies/publications.php.

In various embodiments, where a target species is a protein, the ArrayTube biochip comprises capture binding ligands such as antibodies. A sample is contacted with the biochip, and any target species present in the sample is allowed to bind to the capture binding ligand antibodies. A soluble capture binding ligand or a detection compound such as a horseradish peroxidase conjugated antibody is allowed to bind to the target species. A dye, such as TMB, is then added and allowed to react with the horseradish peroxidase, causing precipitation and a color change that is detected by a suitable detection device. Further description of protein detection using ArrayTube is found in, for example, Huelseweh B, Ehricht R and Marschall H-J, *Proteomics*, 2006, 6, 2972-2981; and ClonDiag, *ArrayTube (AT) Experiment Guideline for Protein-Based Applications*, version 1.2, 2007, all incorporated by reference in their entirety.

Transmission detection and analysis is performed with a ClonDiag AT reader instrument. Suitable reader instruments and detection devices include the ArrayTube Workstation ATS and the ATR 03.

In addition to ArrayTube, the ClonDiag ArrayStrip (AS) can be used. The ArrayStrip provides a 96-well format for high volume testing. Each ArrayStrip consists of a standard 8-well strip with a microarray integrated into the bottom of each well. Up to 12 ArrayStrips can be inserted into one microplate frame enabling the parallel multiparameter testing of up to 96 samples. The ArrayStrip can be processed using the ArrayStrip Processor ASP, which performs all liquid handling, incubation, and detection steps required in array based analysis. In various embodiments, where a protein is detected, a method of using the ArrayStrip to detect the protein comprises conditioning the AS array with buffer or blocking solution; loading of up to 96 sample solutions in the AS wells to allow for binding of the protein; 3× washing; conjugating with a secondary antibody linked to HRP; 3× washing; precipitation staining with TMB; and AS array imaging and optional data storage.

Those skilled in the art will be familiar with numerous additional immunoassay formats and variations thereof which may be useful for carrying out the method disclosed herein. See generally E. Maggio, *Enzyme-Immunoassay*, (CRC Press, Inc., Boca Raton, Fla., 1980); see also U.S. Pat. Nos. 4,727,022; 4,659,678; 4,376,110; 4,275,149; 4,233,402; and 4,230,767.

In general, immunoassays carried out in accordance with the present invention may be homogeneous assays or heterogeneous assays. In a homogeneous assay the immunological reaction usually involves the specific antibody (e.g., anti-biomarker protein antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution Immunochemical labels which may be employed include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays include immunoblotting, immunofluorescence methods, immunoprecipitation, chemiluminescence methods, electrochemiluminescence (ECL) or enzyme-linked immunoassays.

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., $^{35}S$, $^{125}I$, $^{131}I$), enzyme labels (e.g., horseradish peroxidase, alkaline phosphatase), and fluorescent labels (e.g., fluorescein, Alexa, green fluorescent protein, rhodamine) in accordance with known techniques.

Using any of the methods and compositions described herein, a sample can be assayed to determine levels of a biomarker panel. Thus, in one aspect, the invention provides a method of assaying a sample from a patient to determine concentrations of a biomarker panel in the sample. In some embodiments, the method comprises contacting the sample with a composition comprising a solid support comprising a capture binding ligand or capture probe for each biomarker of a biomarker panel.

The invention further provides kits for use in determining gastric health or gastric cancer status for a number of medical (including diagnostic and therapeutic), industrial, forensic and research applications. Kits may comprise a carrier, such as a box, carton, tube or the like, having in close confinement therein one or more containers, such as vials, tubes, ampoules, bottles, pouches, envelopes and the like. In various embodiments, the kits comprise one or more components selected from one or more media or media ingredients and reagents for the measurement of the various biomarkers and biomarker panels disclosed herein. For example, kits of the invention may also comprise, in the same or different containers, one or more DNA polymerases, one or more primers, one or more suitable buffers, one or more nucleotides (such as deoxynucleoside triphosphates (dNTPs) and preferably fluorescently labeled dNTPs) and labeling components. The one or more components may be contained within the same container, or may be in separate containers to be admixed prior to use. The kits of the present invention may also comprise one or more instructions or protocols for carrying out the methods of the present invention. The kits may also comprise a computer or a component of a computer, such as a computer-readable storage medium or device. Examples of storage media include, without limitation, optical disks such as CD, DVD and Blu-ray Discs (BD); magneto-optical disks; magnetic media such as magnetic tape and internal hard disks and removable disks; semi-conductor memory devices such as EPROM, EEPROM and flash memory; and RAM. The computer-readable storage medium may comprise software encoding references to the various therapies and treatment regimens disclosed herein. The software may be interpreted by a computer to provide the practitioner with treatments according to various measured concentrations of biomarkers as provided herein. In various embodiments, the kit comprises a biomarker assay involving a lateral-flow-based point-of-care rapid test with detection of risk thresholds, or a biochip with quantitative assays for the constituent biomarkers.

Methods of Diagnosing and Treating

The compositions and methods of the present invention can be used in the prognosis, diagnosis and treatment of disease in a subject. The invention provides compositions and methods for laboratory and point-of-care tests for measuring biomarkers in a sample from a subject. The invention can be generally applied for a number of different diseases. In exemplary embodiments, the disease is gastric cancer.

The biomarkers and biomarker panels disclosed herein can be used in methods to diagnose, identify or screen subjects that have, do not have or are at risk for having disease; to monitor subjects that are undergoing therapies for disease; to determine or suggest a new therapy or a change in therapy; to differentially diagnose disease states associated with the disease from other diseases or within sub-classifications of disease; to evaluate the severity or changes in severity of disease in a patient; to stage a subject with the disease and to select or modify therapies or interventions for use in treating subjects with the disease. In an exemplary embodiment, the methods of the present invention are used to identify and/or diagnose subjects who are asymptomatic or presymptomatic for a disease. In this context, "asymptomatic" or "presymptomatic" means not exhibiting the traditional symptoms or enough abnormality for disease.

In various embodiments, a method of determining a prognosis of a disease in a subject, diagnosing a disease in a subject, or treating a disease in a subject comprises taking a measurement of a biomarker panel in a sample from the subject.

The term "disease status" includes any distinguishable manifestation of the disease, including non-disease. For example, disease status includes, without limitation, the presence or absence of disease, the risk of developing disease, the stage of the disease, the progression of disease (e.g., progress of disease or remission of disease over time), the severity of disease and the effectiveness or response to treatment of disease.

A "subject" in the context of the present invention is an animal, preferably a mammal The mammal can be a human, non-human primate, mouse, rat, dog, cat, horse, or cow, but are not limited to these examples. In various exemplary embodiments, a subject is human and may be referred to as a patient. Mammals other than humans can be advantageously used as subjects that represent animal models of a disease or for veterinarian applications. A subject can be one who has been previously diagnosed or identified as having a disease, and optionally has already undergone, or is undergoing, a therapeutic intervention for a disease. Alternatively, a subject can also be one who has not been previously diagnosed as having a disease. For example, a subject can be one who exhibits one or more risk factors for a disease, or one who does not exhibit a disease risk factor, or one who is asymptomatic for a disease. A subject can also be one who is suffering from or at risk of developing a disease. In certain embodiments, the subject can be already undergoing therapy or can be a candidate for therapy.

As will be appreciated by those in the art, the biomarkers may be measured in using several techniques designed to achieve more predictable subject and analytical variability.

The term "sample" refers to a specimen or culture obtained from a subject and includes fluids, gases and solids including for example tissue. In various exemplary embodiments, the sample comprises saliva. As will be appreciated by those in the art, virtually any experimental manipulation or sample preparation steps may have been done on the sample. For example, wash steps and/or fragmentation may be applied to a sample. In various embodiments, a biomarker panel is measured directly in a subject without the need to obtain a separate sample from the patient.

In one aspect, the invention provides a method of diagnosing a subject for a disease comprising taking a measurement of a biomarker panel; and correlating the measurement with the disease. The term "correlating" generally refers to determining a relationship between one type of data with another or with a state. In various embodiments, correlating the measurement with disease comprises comparing the measurement with a reference biomarker profile or some other reference value. In various embodiments, correlating the measurement with disease comprises determining whether the subject is currently in a state of disease.

The quantity or activity measurements of a biomarker panel can be compared to a reference value. Differences in the measurements of biomarkers in the subject sample compared to the reference value are then identified. In exemplary embodiments, the reference value is given by a risk category as described further below.

In various embodiments, the reference value is a baseline value. A baseline value is a composite sample of an effective amount of biomarkers from one or more subjects who do not have a disease, who are asymptomatic for a disease or who have a certain level of a disease. A baseline value can also comprise the amounts of biomarkers in a sample derived from a subject who has shown an improvement in risk factors of a disease as a result of treatments or therapies. In these embodiments, to make comparisons to the subject-derived sample, the amounts of biomarkers are similarly calculated. A reference value can also comprise the amounts of biomarkers derived from subjects who have a disease confirmed by an invasive or non-invasive technique, or are at high risk for developing a disease. Optionally, subjects identified as having a disease, or being at increased risk of developing a disease are chosen to receive a therapeutic regimen to slow the progression of a disease, or decrease or prevent the risk of developing a disease. A disease is considered to be progressive (or, alternatively, the treatment does not prevent progression) if the amount of biomarker changes over time relative to the reference value, whereas a disease is not progressive if the amount of biomarkers remains constant over time (relative to the reference population, or "constant" as used herein). The term "constant" as used in the context of the present invention is construed to include changes over time with respect to the reference value.

The biomarkers of the present invention can be used to generate a "reference biomarker profile" of those subjects who do not have a disease according to a certain threshold, are not at risk of having a disease or would not be expected to develop a disease. The biomarkers disclosed herein can also be used to generate a "subject biomarker profile" taken from subjects who have a disease or are at risk for having a disease. The subject biomarker profiles can be compared to a reference biomarker profile to diagnose or identify subjects at risk for developing a disease, to monitor the progression of disease, as well as the rate of progression of disease, and to monitor the effectiveness of disease treatment modalities. The reference and subject biomarker profiles of the present invention can be contained in a machine-readable medium, such as but not limited to, analog tapes like those readable by a VCR; optical media such as CD-ROM, DVD-ROM and the like; and solid state memory, among others.

Measurements of the biomarker panels of the invention can lead a practitioner to affect a therapy with respect to a subject. Thus, the invention provides methods of treating a disease in a subject comprising taking a measurement of a biomarker panel in a sample from the subject, and affecting a therapy with respect to the subject. The terms "therapy" and "treatment" may be used interchangeably. In certain embodiments, the therapy can be selected from, without limitation, initiating therapy, continuing therapy, modifying therapy or ending therapy. A therapy also includes any prophylactic measures that may be taken to prevent disease. Treatment also includes scheduling for a next appointment.

In certain embodiments, treatment comprises administering a disease-modulating drug to a subject. The drug can be a therapeutic or prophylactic used in subjects diagnosed or identified with a disease or at risk of having the disease. In certain embodiments, modifying therapy refers to altering the duration, frequency or intensity of therapy, for example, altering dosage levels.

In various embodiments, effecting a therapy comprises causing a subject to or communicating to a subject the need to make a change in lifestyle, for example, increasing exercise, changing diet, reducing or eliminating smoking and so on. The therapy can also include surgery.

Measurement of biomarker levels allow for the course of treatment of a disease to be monitored. The effectiveness of a treatment regimen for a disease can be monitored by detecting one or more biomarkers in an effective amount from samples obtained from a subject over time and comparing the amount of biomarkers detected. For example, a first sample can be obtained prior to the subject receiving treatment and one or more subsequent samples are taken after or during treatment of the subject. Changes in biomarker levels across the samples may provide an indication as to the effectiveness of the therapy.

To identify therapeutics or drugs that are appropriate for a specific subject, a test sample from the subject can also be exposed to a therapeutic agent or a drug, and the level of one or more biomarkers can be determined Biomarker levels can be compared to a sample derived from the subject before and after treatment or exposure to a therapeutic agent or a drug, or can be compared to samples derived from one or more subjects who have shown improvements relative to a disease as a result of such treatment or exposure. Thus, in one aspect, the invention provides a method of assessing the efficacy of a therapy with respect to a subject comprising taking a first measurement of a biomarker panel in a first sample from the subject; effecting the therapy with respect to the subject; taking a second measurement of the biomarker panel in a second sample from the subject and comparing the first and second measurements to assess the efficacy of the therapy.

Additionally, therapeutic or prophylactic agents suitable for administration to a particular subject can be identified by detecting a biomarker (which may be two or more) in an effective amount from a sample obtained from a subject and exposing the subject-derived sample to a test compound that determines the amount of the biomarker(s) in the subject-derived sample. Accordingly, treatments or therapeutic regimens for use in subjects having a disease or subjects at risk for developing a disease can be selected based on the amounts of biomarkers in samples obtained from the subjects and compared to a reference value. Two or more treatments or therapeutic regimens can be evaluated in parallel to determine which treatment or therapeutic regimen would be the most efficacious for use in a subject to delay onset, or slow progression of a disease. In various embodiments, a recommendation is made on whether to initiate or continue treatment of a disease.

Drug Treatments

In various exemplary embodiments, effecting a therapy comprises administering a disease-modulating drug to the subject. The subject may be treated with one or more disease-modulating drugs until altered levels of the measured biomarkers return to a baseline value measured in a population not suffering from the disease, experiencing a less severe stage or form of a disease or showing improvements in disease biomarkers as a result of treatment with a disease-modulating drug. Additionally, improvements related to a changed level of a biomarker or clinical parameter may be the result of treatment with a disease-modulating drug.

A number of compounds such as a disease-modulating drug may be used to treat a subject and to monitor progress using the methods of the invention. In certain embodiments, the disease-modulating drug comprises The beneficial effects of these and other drugs can be visualized by assessment of clinical and laboratory biomarkers.

Any drug or combination of drugs disclosed herein may be administered to a subject to treat a disease. The drugs herein can be formulated in any number of ways, often according to various known formulations in the art or as disclosed or referenced herein.

In various embodiments, any drug or combination of drugs disclosed herein is not administered to a subject to treat a disease. In these embodiments, the practitioner may refrain from administering the drug or combination of drugs, may recommend that the subject not be administered the drug or combination of drugs or may prevent the subject from being administered the drug or combination of drugs.

In various embodiments, one or more additional drugs may be optionally administered in addition to those that are recommended or have been administered. An additional drug will typically not be any drug that is not recommended or that should be avoided. In exemplary embodiments, one or more additional drugs comprise one or more glucose lowering drugs.

Decision Matrices

The therapy chosen by a practitioner can depend on the concentrations of biomarkers determined in a sample. In various exemplary embodiments, the therapy depends on which category from a range of categories particular to each biomarker the measured concentration of each biomarker falls in. In various exemplary embodiments, the therapy depends on the combination of risk levels for different symptoms or diseases that are indicated by a biomarker panel.

With respect to concentration measurements of a biomarker, the term "category" refers to a subset of a partition of the possible concentrations that a biomarker may have. Each category may be associated with a label or classification chosen by the practitioner. The labels may be referred to, for example, the risk level of an individual for having or being subject to a disease state. The categories and labels may be derived from the current literature or according to the findings of the practitioner.

Each biomarker of a biomarker panel can thus be associated with a discrete set of categories, for example, risk categories. Combining one category from each biomarker forms a "decision point." In various exemplary embodiments, the complete set of decision points comprises all possible n-tuples of categories, wherein n is the number of biomarkers in the biomarker panel. This complete set will have $m_1 \times m_2 \times \ldots m_n$ possible decision points, wherein $m_i$ is the number of categories for biomarker i.

Every decision point can be associated with a condition or a disease state, which is not necessarily unique. That is, one or more decision points can be associated with the same disease state. The association of every possible decision point with a condition or disease state can be referred to as a "disease classification matrix" or a "disease classification tree." Thus, by correlating a measurement of a biomarker panel with a decision point, the practitioner can classify the condition or disease state of a patient.

Every decision point can also be associated with a particular therapy, which is not necessarily unique. That is, one or more decision points can be associated with the same therapy. The association of every possible decision point with one or more therapies can be referred to as a "therapy decision matrix" or "therapy decision tree."

Each decision point can be associated with more than one type of information. For example, both disease state and therapy can be indicated by a decision point.

The articles "a," "an" and "the" as used herein do not exclude a plural number of the referent, unless context clearly dictates otherwise. The conjunction "or" is not mutually exclusive, unless context clearly dictates otherwise. The term "include" is used to refer to non-limiting examples.

EXAMPLES

Example 1

Salivary Transcriptomic Profiling and Analysis

After collection, saliva was centrifuged at 2600 g at 4° C. for 15 minutes. Saliva supernatant was separated from the pellet. Total RNA from the saliva supernatant samples of 63 gastric cancer patients and 31 healthy controls were extracted using an RNA extraction kit (Qiagen RNeasy Mini Kit from Qiagen). DNase treatment (TURBO™ DNase, Ambion) was used to remove contaminating DNA. 90 µL of extracted total RNA (out of 100 µL) was concentrated to 10 µL and then linearly amplified using the RiboAmp RNA Amplification kit (Molecular Devices, Sunnyvale, Calif.). After purification, cDNA was in vitro transcribed and biotinylated using GeneChip Expression 3'—Amplification Reagents for in vitro transcription labeling (Affymetrix, Santa Clara, Calif.). Equal amounts of labeled RNA (~20 µg) were subsequently fragmented and sent to the UCLA microarray core facility for chip hybridization and scanning. The Affymetrix Human Genome U133 Plus 2.0 Array, which represents >47,000 transcripts and variants, was applied in the salivary transcriptomic profiling.

The CEL files from all datasets were imported into the statistical software R 2.7.0. using Bioconductor 2.2. The analysis was performed as follows: the Probe Logarithmic Intensity Error Estimation (PLIER) expression measures were computed after background correction and quantile normalization for each microarray dataset. Probeset-level quantile normalization was performed across all samples to make the effect sizes similar among all datasets. Finally, for every probeset, two-sample t-test was applied to identify differential expression. After obtaining the estimates and the p-values of each probeset, the p-values were corrected for false discovery rate (FDR). Genes were selected at the FDR level of 0.05, and with cancer effect size >2 fold change between cancer and normal samples. The twelve mRNA biomarkers discovered are displayed in Table 1.

TABLE 1

Salivary mRNA markers

| Gene Symbol | Gene name |
| --- | --- |
| ANXA1 | Annexin A1 |
| CSTB | Cystatin B or Stefin B |
| SEMA4B | Semaphorin 4B |
| S100A10 | S100 calcium binding protein A10 |
| PPL | Periplakin |
| SPINK7 | Serine peptidase inhibitor, Kazal type 7 |
| EROL-like | EROL-like |
| RANBP9 | RAN binind protein 9 |
| CD24 | CD24 |
| KRT6A | Keratin 6A |
| KRT4 | Keratin 4 |
| EIF3G | Eukaryotic translation initiation factor 3, subunit G |

The biomarker candidates generated by microarray profiling were verified by real-time quantitative RT-PCR on the same set of samples used for the microarray analysis. qPCR primers were designed using Primer Express 3.0 software (Applied Biosystems, Foster City, Calif.), with a melting temperature of 58-61° C., and synthesized by Sigma-Genosys (Woodlands, Tex.). The amplicons were intron spanning whenever possible. Amplicon lengths were around 90-125 bp for the outer primer pairs used in pre-amplification and 50-80 bp for the inner primer pairs used in qPCR analysis.

Total RNA was reverse-transcribed using reverse transcriptase and gene-specific primers using the following thermal cycling conditions: 60° C. for 1 min, 50° C. for 30 min, 95° C. for 2 min, and 15 cycles of 95° C. for 15 sec, 50° C. for 30 sec, 60° C. for 10 sec, and 72° C. for 10 sec. These steps were followed with a final extension of 72° C. for 5 min and cooling to 4° C. The pre-amplified product was cleaned up using ExoSAP-IT® (USB Corporation) and then diluted ¹⁄₁₀ with water. 2 µL template was used for qPCR.

qPCR was carried out in a 384-well plate in reaction volumes of 10 µl using SYBR Green 1 Master Mix (Roche, San Francisco, Calif.). Initial denaturing was performed at 95° C. for 5 min, followed by 40 cycles of 95° C. for 10 sec, 60° C. for 10 sec, and 72° C. for 10 sec for amplification, and then 95° C. for 5 sec, 65° C. for 1 min, and 97° C. for detecting the melting curve on the Roche LightCycler 480 II (Roche, San Francisco, Calif.). All qPCRs were performed in duplicate for all candidate mRNA. The specificity of the PCR was confirmed according to the melting curve of each gene, and the average threshold cycle (Ct) was examined.

For mRNA qPCR experiments, the data analysis was performed using the $2^{-\Delta Ct}$ method, where GAPDH is used as the reference gene. The qPCR based gene expression values between two groups were compared using the non-parametric Wilcoxon test. To normalize for RNA input, qPCR was performed for GAPDH, which is a commonly used housekeeping gene for mRNA normalization in cells. Raw data were normalized by subtracting GAPDH Ct values from the marker Ct values to provide ΔCt and then analyzed with the use of stats, utilities packages from R 2.7.0 and the ROC package from Bioconductor 2.2. Statistical comparisons were made with the use of the Mann-Whitney U test with consideration of two different distributions for control and lung cancer groups. Biomarkers that were best differentiated between groups of subjects (P value<0.05) were identified and compared by the Area Under Curve (AUC) value. The AUC is based on constructing a receiver operating characteristic (ROC) curve which plots the sensitivity (y-axis in our analysis) versus one minus the specificity (x-axis in our analysis). The AUC value is computed by numerical integration of the ROC curve. The typical range for this value is between 0.5 to 1.0. The value of 0.5 indicates that the biomarker has no diagnostic utility, e.g., that the biomarker is no better than a coin toss, and 1.0 would indicate perfect diagnostic accuracy.

Example 2

Salivary Proteomic Profiling and Analysis

After collection, saliva was centrifuged at 2600 g at 4° C. for 15 minutes. Saliva supernatant was separated from the pellet and stored at −80° C. until further analysis. By taking equal amount of protein from each individual sample (20 gastric cancer samples and 20 healthy control samples), proteins from every four samples were pooled into one sample in the cancer group and healthy control group, respectively. These result in 5 pooled cancer samples and 5 pooled healthy control samples. All the 10 pooled samples were subjected to amylase removal by using starch column. Two global internal standard (GIS) pooled saliva samples were made from all the 10 pooled samples for the comparison between two TMT-6plex experiments.

For one TMT-6plex experiment, the 100 μg proteins in each saliva sample were dissolved in 45 μL of 200 mM TEAB, adjust the sample to a final volume of 100 μL with ultrapure water. With adding 5 μL 200 mM TCEP, the reaction was performed for 1 hour at 55° C. An amount of 5 μL of 375 mM IAA was then added, add the mixtures were reacted for 30 min in the dark at RT. An amount of 5 μL of freshly prepared trypsin at 0.5 μg/uL concentration in TEAB (200 mM) were added. The digestion was performed overnight at 37° C. In group A, 1 GIS, 3 healthy control samples and two cancer samples were labeled by TMT with reporters at m/z=126.1, 127.1, 128.1, 129.1, 130.1, 131.1, respectively. In group B, 1 GIS, the left 3 cancer samples and 2 healthy controls samples were labeled by another set of TMT with reporters at m/z=126.1, 127.1, 128.1, 129.1, 130.1, 131.1, respectively. After 1 h of reaction at RT, 8 μL of 5% hydroxylamine (w/V) was added in each tube and mix for 15 min. The six samples in group A and group B were pooled in a new tube, respectively, and dried for storage at −80° C.

The pooled TMT-labeled saliva samples were fractionated by cation-exchange chromatography using a flow rate at 0.8 mL/min on a 4 6×250 mm, (5 μm, 125 Å) TSK gel CM-2SW column (Tosoh Bioscience, Stuttgart, Germany). The gradient was run as follows: 0-3 min 100% A (10 mM Ammonium Acetate, 25% CH$_3$CN, adjusted to pH=3 with HAC), then to 100% B (200 mM Ammonium Acetate, 25% CH$_3$CN, adjusted to pH=3 with HAC) at 15 min. Fractions were collected every minute. The fractions were dried under vacuum and stored at −80° C. for further LC-MS/MS analysis.

Peptides in each fraction were rehydrated in 2% (v/v) acetonitrile/ 0.1% (v/v) formic acid in water and injected with an autosampler (Eksigent NanoLC-2D). Peptides were first enriched on a reverse phase trap column (ProteoPep II, 100 μm×2.5 cm, C18, 5 μm, 300 Å, New Objective, USA) and then eluted to analytical column (Magic C18AQ, 100 μm×15 cm, 3 μm, 200 Å, Michrom Bioresources, USA). The mobile phase consisted of buffer (A) 2% acetonitrile and 0.1% formic acid in water, and buffer (B) 2% water and 0.1% formic acid in acetonitrile. A flow rate of 250 nL/min was applied for the separation of peptides for 140 min. The gradient run was followed: 0-1 min, 2% B, then to 30% B at 90min, 80% B at 110 min, and 2% B at 140 min. The mass spectrometer voltage was set to 1800V and the heated capillary was kept at 180° C. All mass spectra was acquired in the positive ionization mode with an m/z scan range of 350-2000. The LTQ-Orbitrap XL (Thermo Fisher Scientific) was operated in a top 4 configuration at 60 000 resolving power (defined by m/Δm50%) for a full scan, with enabled charge state screening, monoisotopic precursor selection enabled, and +1, and unassigned charge states rejected. After the master scan, the three most intense ions were subjected for collision-induced dissociation (CID) fragmentation using an isolation window of 3.0, collision energy of 30, default charge state of 2 and activation time of 30 ms. Fragmentation of three most intense TMT reporter ions was achieved with higher energy collisional dissociation (HCD) fragmentation at 7500 resolving power in the LTQ-Orbitrap using an isolation window of 2, collision energy of 40, default charge state of 2 and activation time of 30 ms.

LC-MS/MS data analysis was performed with Qual Brower (v2.0.7) and Proteome Discoverer (v1.1) interfaced SEQUEST (human IPI database v3.78). Up to two missed cleavage sites were allowed during the database search. Peptide and protein identification was filtered with charge state dependent cross correlation (Xcorr)≥2.0 and peptide rank No. 1 with requiring at least two peptides per protein. The filters allowed a 95% confidence level of protein identification with less than 5% false discovery rate. The Reporter Ions Quantitizer in the Proteome Discoverer was used to quantify the TMT reporter ion intensities at 126.13-131.14 m/z. Protein identification and quantification intensity ratios were exported to Microsoft Excel software. P value between the cancer and control groups was calculated based on t-test and p<0.05 was used as cut-off for significance. In total, 519 proteins were identified with quantification. Among them, 48 proteins showed significant difference between normal controls and gastric cancer patients (p<0.05). Seven proteins exhibited up-regulation and 41 proteins exhibited down-regulation in the cancer group compared to normal controls.

Based on fold change and P value, three proteins were selected for verification, including Triosephosphate isomerase 1, Cystatin-B, and Deleted in malignant brain tumors 1 protein. In order to verify these candidate biomarkers, ELISA was used to quantify the three proteins on the original sample set. The three proteins are shown in Table 2.

TABLE 2

Salivary protein markers

| Protein Symbol | Protein name |
|---|---|
| TPI1 | Triosephosphate isomerase 1 |
| CSTB | Cystatin-B |
| DMBT1 | Deleted in malignant brain tumors 1 protein |

The ELISA tests for Triosephosphate isomerase 1, Cystatin B, and Deleted in malignant brain tumors 1 protein (Antibodies-online, Atlanta, Ga., USA) were performed according to the manufacturers' instructions. All saliva samples were diluted 10 times with sample diluents for all three proteins. The distribution of these three proteins in cancer and control groups shows significant difference with p value 0.012, 0.035, 0.0038, respectively.

Example 3

Saliva Microbial Biomarkers

After collection, saliva was centrifuged at 2600 g at 4° C. for 15 minutes. The pellet was separated from the saliva supernatant and DNA from the saliva pellet was extracted using UltraClean Microbial DNA Isolation Kit (MO BIO Laboratories Inc.). The protocol followed the product manual. PCR amplification using 16S universal primers was performed in Forsyth Institute, followed by hybridization on the HOMIM microarray. Selection of bacteria candidates: based on the fold change and statistical analysis (Wilcoxon signed-rank test), analysis from the UCLA Wong lab and Forsyth Institute were combined. Twenty-eight candidates were selected for differentiation between disease and control.

Confirmation by real time PCR: quantities of bacteria species in the original DNA samples were determined using real time PCR. Specific primers were designed for all species and real-time PCR are performed to check the bacterial quantity between cancer and controls. Their relative quantities in disease and control samples were significant different (p<0.05). Four bacterial biomarkers shown in Table 3 were verified and were less abundant in the cancer samples in comparison to controls.

TABLE 3

Salivary microbial biomarkers
Strain name

*Neisseria* sp strain
B33KA_ot020_Y56
*Eikenella corrodens* and *Kingella denitrificans* and sp clone
DE012_0t012_577_582_AD98
*Streptococcus australis* and sp clone
FN04_ot065_073_AB83
*Fusobacterium* all species_AD99

Example 4

Saliva Micro-RNA Biomarkers

After collection, saliva was centrifuged at 2600 g at 4° C. for 15 minutes. Saliva supernatant was separated from the pellet. Total RNAs from the saliva supernatant samples of 10 gastric cancer patients and 10 healthy controls were extracted using an RNA extraction kit (mirVana PARIS from Ambion). DNase treatment (DNase I, Qiagen) was used to remove contaminating DNA during RNA extraction.

3 µl of extracted total RNA (1-10 ng) was reverse transcribed and pre-amplified miRNAs using the Taqman MicroRNA Reverse Transcription kit, Taqman PreAmp Master mix, and Megaplex Primers (Applied Biosystems, Foster City, Calif.). Prior to running the reaction, undiluted pre-amp product was mixed with Taqman Universal PCR Master Mix with no UNG (Applied Biosystems, Foster City, Calif.). 105 µl was loaded into each well of the Taqman Human MicroRNA Array cards, which were then spun down and run on the Applied Biosystems 7900HT Fast Real-Time PCR instrument containing a special card holder (Applied Biosystems, Foster City, Calif.). Using default TLDA setting and FAM as a reporter, the reaction was run at 95° C. for 10 minutes to activate the enzyme and then followed with 40 cycles at 95° C. for 15 sec and at 60° C. for 60 sec. The threshold cycle (Ct) was examined.

Data analysis was performed using the $2^{-\Delta Ct}$ method. RNA polymerase III transcribed U6 snRNA was used as the reference gene. The qPCR based gene expression values between the two groups were compared using both the t-test and non-parametric Wilcox test. Data normalization was performed by using U6 snRNA as an endogenous control to correct for variation. Data normalization was performed using RQ manager 1.2.1 and Data Assist v3.0 from Applied Biosystems. After obtaining the estimates and p-values of each data set, the p-values were corrected for false discovery rates (FDR). Potential miRNA genes were selected for verification at FDR levels of less than 0.05 and had a fold change difference of >2 between cancer and normal control samples.

The biomarker candidates generated by the Taqman MicroRNA Array cards were verified by real-time quantitative RT-PCR using Taqman MicroRNA assays on the same set of samples. Taqman MicroRNA assays containing the specific miRNA genes were ordered from Applied Biosystems.

Total RNA was reverse-transcribed with the Taqman MicroRNA Reverse Transcription kit (Applied Biosystems, Foster City, Calif.) using the following thermal cycling conditions: 16° C. for 30 min, 42° C. for 30 min, 85° C. for 5 min, and then cooled to 4° C. Pre-amplification was performed with Taqman PreAmp Master mix (Applied Biosystems, Foster City, Calif.) using the following thermal cycling conditions: 95° C. for 10 min, 55° C. for 2 min, 72° C. for 2 min, 12 cycles at 95° C. for 15 sec and 60° C. for 4 min, then 99.9 ° C. for 10 min to inactivate the enzyme, and then ending at 4° C.

PCR was carried out in a 384 well plate in reaction volumes of 10 µl using Taqman Universal PCR Master Mix with no UNG (Applied Biosystems, Foster City, Calif.). Initial denaturing was performed for 10 min at 95° C. and then followed by 40 cycles of 95° C. for 15 sec and 60° C. for 1 min on the Roche LightCycler 480 II (Roche, San Francisco, Calif.). All qPCRs were performed in duplicate for all candidate miRNA. The average threshold cycle (Ct) was examined.

For miRNA qPCR experiments, U6 snRNA was used as the reference gene. The qPCR based gene expression values between the cancer and normal control groups were compared using the t-test. Raw miRNA Ct values were normalized by subtracting the U6 snRNA Ct value from the potential miRNA Ct value. miRNA biomarkers that were best differentiated between the cancer and normal control groups with P value<0.05 were considered verified.

The six micro-RNA markers are provided in Table 4.

TABLE 4

Salivary micro-RNA markers.
Micro-RNA name miR-140-5p
miR-374a
miR-454
miR-15b
miR-28-5p
miR-301a The examples set forth above are provided to give those of ordinary skill in the art a complete disclosure and description of how to make and use the embodiments of the compositions, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

The invention claimed is:

1. A method of diagnosing and treating gastric cancer, the method comprising:
   obtaining a saliva sample of a human subject at risk of having gastric cancer;
   separating the saliva sample into two saliva sample portions, wherein the first saliva sample portion is a saliva supernatant and wherein the second saliva sample portion is a saliva pellet;
   measuring the level of at least four mRNA biomarkers and at least one micro-RNA biomarker in the saliva supernatant, wherein the at least four mRNA biomarkers comprises at least four biomarkers are selected from the group consisting of Cystatin/Stefin B (CSTB), Semaphorin 4B (SEMA4B), S100 calcium binding protein A10 (S100A10), and Kazal type 7 (SPINK7), and wherein the at least one micro-RNA biomarker comprises miR-140-5p;
   comparing the levels of the at least four mRNA biomarkers and the at least one micro-RNA biomarker measured in the saliva supernatant with a control level of the at least four mRNA biomarkers and the at least one micro-RNA biomarker, wherein the control level of the at least four mRNA biomarkers and the at least one micro-RNA biomarker is a level of the at least four mRNA biomarkers and the at least one micro-RNA biomarker in a healthy population, wherein a statistically significant difference between the at least four mRNA biomarkers and the at least one micro-RNA biomarker measured in the saliva supernatant and the control level is indicative of gastric cancer;
   diagnosing gastric cancer upon detection of a statistically significant difference between the level of the at least four mRNA biomarkers and the at least one micro-RNA biomarker measured in the saliva supernatant and the control levels of the at least four mRNA biomarkers and the at least one micro-RNA biomarker; and
   administering an effective amount of a treatment regimen to treat gastric cancer, wherein the treatment regimen is selected from the group consisting of chemotherapy, hormonal therapy, radiotherapy, and immunotherapy, to a human subject diagnosed as having gastric cancer.

2. The method of claim 1, further comprising measuring the level of at least one additional mRNA biomarker selected from the group consisting of Annexin 1 (ANXA1), Periplakin (PPL), EROL-like (ERO1B), RAN binding protein 9 (RANBP9), CD24, Keratin 6A (KRT6A), Keratin 4 (KRT4), and eukaryotic translation initiation factor 3 subunit G (EIF3G).

3. The method of claim 1, further comprising measuring the level of at least one additional micro-RNA biomarker selected from the group consisting of miR-374a, miR-454, miR-15b, miR-28-5p, and miR-301a.

* * * * *